United States Patent [19]

Sarnoff

[11] 4,292,311

[45] Sep. 29, 1981

[54] CYANIDE ANTIDOTE

[76] Inventor: Stanley J. Sarnoff, 7507 Hampden La., Bethesda, Md. 20034

[21] Appl. No.: 219,852

[22] Filed: Dec. 23, 1980

[51] Int. Cl.³ .................... A61K 33/04; A61K 33/02
[52] U.S. Cl. .................................... 424/162; 424/10; 424/166
[58] Field of Search ................ 424/10, 166, 162, 164

[56] References Cited

PUBLICATIONS

Nonomura et al.-Chem. Abst. vol. 86 (1977) p. 145571x.
Rozenberg-Chem. Abst. vol. 66 (1967) p. 84258p.

*Primary Examiner*—Sam Rosen
*Attorney, Agent, or Firm*—Cushman, Darby & Cushman

[57] ABSTRACT

As an antidote for cyanide poisoning there is injected hydroxylamine hydrochloride. This is followed by treatment with thiosulfate. The hydroxylamine hydrochloride can also be employed as a respiratory stimulant in treating other illnesses.

13 Claims, No Drawings

CYANIDE ANTIDOTE

BACKGROUND OF THE INVENTION

Hydrogen cyanide is highly toxic. It is a known attack agent in chemical warfare. It is also a very important chemical for use in numerous industrial processes. Its salts, e.g., sodium cyanide and potassium cyanide are also used in many industrial processes and also are highly toxic.

When cyanide intoxication is experienced, the cyanide interferes with the performance of the cytochrome oxidase system thereby inhibiting the efficiency of oxygen transport to the tissues. Therapeutic attempts to counteract cyanide poisoning have largely consisted of the introduction of compounds such as the nitrites like sodium nitrite. More recently, dimethylaminophenol has been used in order to produce methemoglobin. As a result of cyanide's greater affinity for methemoglobin than for the cytochrome oxidase system, it leaves the latter and forms cyanomethemoglobin thereby restoring, at least partially, the oxygen transport function of the cytochrome oxidase system. Subsequently therapy with thiosulfate, e.g., sodium thiosulfate, converts the cyanide to thiocyanate which is then excreted by the kidney.

For the effective treatment of cyanide poisoning, it is important that hemoglobin be rapidly converted to methemoglobin. It is also important that the effect of the treatment be long lasting, e.g., 30 to 60 minutes or even longer. While sodium nitrite has been successfully used, as indicated supra, it has the disadvantage that it is relatively slow in converting hemoglobin to methemoglobin.

Dimethylaminophenol very rapidly converts hemoglobin to methemoglobin but has the disadvantage that it is relatively expensive, the intramuscular injection hurts, causes an abscess and may be difficult to stabilize in an appropriate injector.

It has long been known that hydroxylamine and hydroxylamine hydrochloride cause methemoglobinemia, e.g., see J. Boil. Chem., Vol. 143, 331 (1942) and Merck Index, 8th and 9th Edition. However, no one has shown that hydroxylamine or hydroxylamine hydrochloride could be used as a therapeutic drug to counteract cyanide poisoning.

SUMMARY OF THE INVENTION

It has now been found that hydroxylamine hydrochloride can be used as a therapeutic in the treatment of cyanide poisoning. Cyanide poisoning can also be caused by potassium cyanide or hydrogen cyanide. The injection of the hydroxylamine hydrochloride can take place in various ways, e.g., parenterally. Intravenous injection is more rapidly effective than intraperitoneally in converting hemoglobin to methemoglobin. Injection intramuscularly may even be superior to intravenous injection, since it has been found that intramuscular injection of hydroxylamine hydrochloride acts as a respiratory stimulant. This may be important since one of the effects of cyanide poisoning is apnea (cessation of breathing). Consequently, it is desirable that a therapeutic for cyanide poisoning also acts as a respiratory stimulant when possible.

It has been found that in treating cats that with a dose of hydroxylamine hydrochloride of 8 mg/kg of body weight the methemoglobin content went up to about 37% of the total hemoglobin in 2 minutes and was still above 20% after 1.75 hours. With a dosage of hydroxylamine hydrochloride of 6 mg/kg, the methemoglobin content went up to 22% in 2 minutes and was 10% after 2 hours. With a dosage of hydroxylamine hydrochloride of 2 mg/kg the methemoglobin content went to 9% in 4 minutes, to a maximum of 10% in 15 minutes, was still 8% after 1½ hours and was 4% after 2 hours.

In contrast using sodium nitrite at a dosage of 6 mg/kg the methemoglobin was 7% after 1 minute, was still at this level after 2 minutes, increase to a maximum of 12% after 25 minutes and was 8% after 2 hours.

Unlike hydroxylamine, hydroxylamine hydrochloride is stable in solution. Also as indicated above, it is long acting, in fact well beyond 30–60 minutes and for as much as 2 hours or longer.

The hydroxylamine hydrochloride can be used to treat animals, e.g., mammals for veterinary use, e.g., in treating dogs, cats, horses, or cows or to treat humans for cyanide poisoning or as a respiratory stimulant (e.g., not only in the case of cyanide poisoning but wherever a respiratory stimulant is needed, e.g., in barbituate poisoning) in a wide range of dosages, e.g., 1 to 30 mg/kg of body weight, usually 5 to 10 mg/kg.

The concentration of the hydroxylamine hydrochloride is not critical. It has been found, for example, that a 17.5% solution is stable and can be employed. When using an injector which has a maximum delivery of 3 ml there must be used a concentration which will give the required dosage (i.e., 1 to 30 mg/kg. In a duplex injector which can deliver up to 6 ml of material the concentration can be reduced and still obtain the same dosage.

In the treatment of cyanide poisoning, after the injection with the hydroxylamine hydrochloride, there is either simultaneously or subsequently injected sodium thiosulfate or potassium thiosulfate to pull the cyanide off the cyanomethemoglobin. While the injection of the thiosulfate can be carried out in various ways, it also is preferably injected intravenously or alternatively may be injected intramuscularly. The dosage of thiosulfate is that previously used in the treatment of cyanide poisoning, e.g, 50 ml of a 25% aqueous solution of corresponding amounts of 5 to 50% solution. The sodium thiosulfate (or potassium thiosulfate) can be employed in an amount up to its solubility limit at 0° C.

When the hydroxylamine hydrochloride and sodium thiosulfate are employed simultaneously they can either be employed (a) in two separate injectors, (b) in two separate chambers of a single injector, or (c) as a simple mixture in one injection.

The thiosulfate is usually employed in an amount of 150 to 200 mg/kg of body weight.

DETAILED DESCRIPTION

In treating a 40 lb dog which has been subjected to cyanide poisoning (with sodium cyanide) there is intramuscularly injected from an injector about 1.0 ml of a 17.5% aqueous hydroxylamine hydrochloride solution followed by the injection intravenously of about 13 ml of 25% aqueous sodium thiosulfate solution.

A 150 lb human would require about 4 ml of the 17.5% hydroxylamine hydrochloride solution and 50 ml of the 25% aqueous sodium thiosulfate solution.

The process can comprise, consist essentially of, or consist of the steps set forth with the recited materials.

What is claimed is:

1. A process of treating a mammal which has had cyanide poisoning with an antidote therefor comprising injecting the mammal with sufficient hydroxylamine hydrochloride solution to increase the mammal's methemoglobin concentration and to convert the cyanide to cyanomethemoglobin.

2. A process according to claim 1 wherein the hydroxylamine hydrochloride is employed in an amount of 1 to 20 mg/kg of body weight.

3. A process according to claim 2 wherein the hydroxylamine hydrochloride is employed in an amount of 5 to 10 mg/kg of body weight.

4. A process according to claim 3 including the step of also injecting into the mammal sufficient sodium thiosulfate to convert the cyanide portion of the cyanomethemoglobin to thiocyanate.

5. A process according to claim 4 wherein there is employed the thiosulfate in an amount of 150–200 mg/kg of body weight.

6. A process according to claim 2 including the step of also injecting into the mammal sufficient sodium thiosulfate to convert the cyanide portion of the cyanomethemoglobin to thiocyanate.

7. A process according to claim 5 wherein there is employed the thiosulfate in an amount of 150–200 mg/kg of body weight.

8. A process according to claim 1 including the step of also injecting into the mammal sufficient sodium thiosulfate to convert the cyanide portion of the cyanomethemoglobin to thiocyanate.

9. A process according to claim 8 wherein there is employed the thiosulfate in an amount of 150–200 mg/kg of body weight.

10. A process according to claim 1 including the step of also injecting into the mammal sufficient thiosulfate to convert the cyanide portion of the cyanomethemoglobin to thiocyanate.

11. The process according to claim 10 wherein the thiosulfate is sodium thiosulfate or potassium thiosulfate.

12. A process according to claim 11 comprising simultaneously injecting the hydroxylamine hydrochloride and the thiosulfate.

13. A process according to claim 11 comprising injecting the hydroxylamine hydrochloride prior to injecting the thiosulfate.

* * * * *